United States Patent [19]

Descamps et al.

[11] 4,124,710
[45] Nov. 7, 1978

[54] ACETAMIDOXIME DERIVATIVES AND USE THEREOF

[75] Inventors: Marcel Descamps, Rosieres; Alex Areschka, Brussels, both of Belgium

[73] Assignee: Labaz, Paris, France

[21] Appl. No.: 748,725

[22] Filed: Dec. 9, 1976

[51] Int. Cl.² .............. C07D 295/12; A61K 31/535
[52] U.S. Cl. .................... 424/248.56; 424/250; 424/267; 424/274; 424/285; 260/326.5 D; 260/346.73; 544/153; 544/376; 546/196
[58] Field of Search ............. 260/247.5 H, 268 BC, 260/293.58, 326.5 D, 346.73; 544/153; 424/248.56, 250, 267, 274, 285

[56] References Cited
FOREIGN PATENT DOCUMENTS 1,380,145  1/1975  United Kingdom ............... 260/247.5

Primary Examiner—Henry R. Jiles
Assistant Examiner—R. W. Ramsuer
Attorney, Agent, or Firm—Warren D. McPhee

[57] ABSTRACT

The invention relates to acetamidoxime derivatives represented by the general formula:

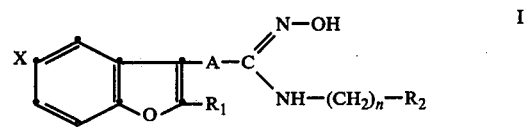

and the pharmaceutically acceptable acid addition salts thereof, wherein $R_1$ represents a branched- or straight-chain alkyl group containing from 1 to 4 carbon atoms or a phenyl group, A represents one of the groups:

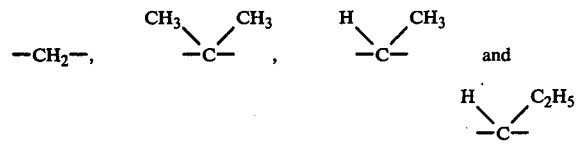

, $R_2$ represents
an amino group such as, for example, a dimethylamino, diethylamino, di-n-propylamino, di-n-butylamino, pyrrolidino, morpholino, piperidino or heptamethyleneimino group or a 1-piperazino group substituted in the 4-position by a straight-chain alkyl group containing from 1 to 4 carbon atoms, X represents a hydrogen or chlorine atom or a methoxy group and $n$ is the integer 2 or 3.

The compounds of formula I have been found to be potentially useful in the treatment of disorders of arterial pressure.

9 Claims, No Drawings

ACETAMIDOXIME DERIVATIVES AND USE THEREOF

This invention relates to heterocyclic compounds and is concerned with acetamidoxime derivatives of benzofuran and pharmaceutical compositions containing them and with a process for preparing the said acetamidoxime derivatives.

The compounds of the invention, which can exist in racemic form or in the form of their optically active isomers, can be represented by the general formula:

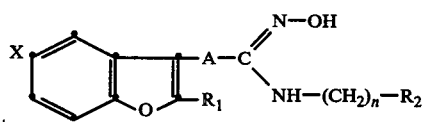   I wherein $R_1$ represents a branched- or straight-chain alkyl group containing from 1 to 4 carbon atoms or a phenyl group; A represents one of the groups:

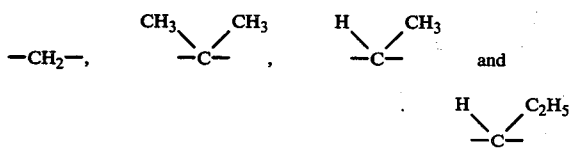

$R_2$ represents an amino group, such as for example a dimethylamino, diethylamino, di-n-propylamino, di-n-butylamino, pyrrolidino, morpholino, piperidino or heptamethyleneimino group or a 1-piperazine group substituted in the 4-position by a straight-chain alkyl group containing from 1 to 4 carbon atoms; X represents a hydrogen or chlorine atom or a methoxy group; and $n$ is the integer 2 or 3.

The pharmaceutically acceptable acid addition salts of the compounds of formula I are included within the scope of the invention.

The compounds of formula I can be prepared by ring opening of a 3,4-disubsituted-1,2,4-$\Delta^2$-oxadiazol-5-one represented by the general formula:

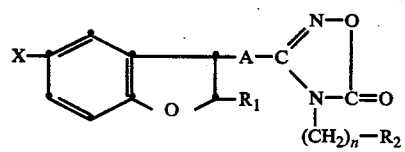   II or of an acid addition salt thereof, in which formula $R_1$, $R_2$, A, X and $n$ have the same meanings as in formula I. The ring opening can be accomplished using a known procedure, for example by heating the compound in an aqueous alcoholic medium in the presence of a base, for example sodium hydroxide.

The compounds of formula II can be prepared by reacting, in an organic medium such as, for example, anhydrous acetone containing a small quantity of methyl alcohol, and in the presence of a base such as, for example, anhydrous potassium carbonate, a 3-substituted 1,2,4-$\Delta^2$-oxadiazol-5-one of the general formula:

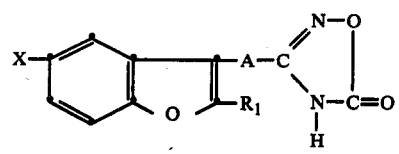   III in which $R_1$, A and X have the same meanings as in formula I, with a chloroalkylamine, preferably in the form of its hydrochloride salt, represented by the general formula:

   IV

Cl-$(CH_2)_n$-$R_2$ in which $R_2$ and $n$ have the same meanings as in formula I.

The compounds of formula IV are already known.

The compounds of formula III can be prepared using known procedures, for example by reacting, in absolute ethanol containing a base such as sodium ethylate, an amidoxime derivative represented by the general formula:

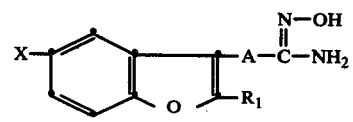   V or an acid addition salt thereof, in which formula $R_1$, A and X have the same meanings as in formula I, with anhydrous diethyl carbonate.

The compounds of formula V can be prepared by using methods widely described in the literature. One particularly advantageous method consists of reacting, in an alcoholic medium containing a base, such as sodium methylate or sodium ethylate, a compound represented by the general formula:

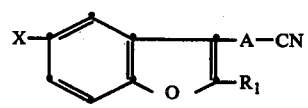   VI in which $R_1$, $R_2$ and X have the same meanings as in formula I, with hydroxylamine hydrochloride.

The compounds of formula VI in which A represents the group —$CH_2$— are already known, having been described by ARESCHKA et al in Chimie Therapeutique 7, 337 (1972), or may be prepared by the processes described in the said publication.

The compounds of formula VI in which A represents the group:

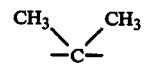

can be prepared by reacting a compound of formula VI in which A represents the group —$CH_2$— with a group of the formula $CH_3$-Hal in which Hal represents an atom of chlorine, bromine or iodine.

The compounds of formula VI in which A represents either of the groups:

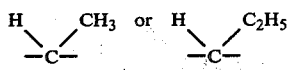

can be prepared by alkylating, in liquid ammonia containing sodium amide prepared in situ, a compound of the general formula:

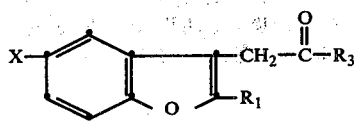

in which $R_1$ and X have the same meanings as in formula I and $R_3$ represents a methoxy or ethoxy group, by means of methyl iodide or ethyl iodide and reducing the ester function of the compound so obtained to a nitrile function, the reduction being carried out using a known procedure.

The compounds of formula VII can be prepared by known procedures from the compounds of formula VI in which A represents the group —$CH_2$—.

The compounds of the invention have been found to possess useful pharmacological properties capable of rendering them of considerable value in the treatment of disorders of the cardiovascular system, characterized by high blood pressure or low blood pressure.

Another object of the invention is therefore a method of treatment pathological disorders of arterial pressure and, in particular hypertension in a subject in need of such treatment by administering to the said subject at least one compound of formula I or a pharmaceutically acceptable acid addition salt thereof.

The predominant types of hypertension are essential and malignant hypertension and there is no specific therapy for these diseases, individual cases varying widely in response to various drugs.

There are therefore many anti-hypertensive agents which are used to treat the different types of hypertension.

Amongst them, ganglionic blocking agents are known to exert a gangioplegic effect in that they interrupt the sympathicotonic impulses thus causing relaxation of the vascular walls. This phenomenon may be dangerous in cases where the patient requires increased tonicity of the vascular walls as a result of, for example, a change of position. As may be seen further on, the compounds of the invention are devoid of any ganglioplegic effects.

Other anti-hypertensive compounds, such as the veratrum alkaloids, are characterized by a rather narrow margin between their therapeutic and toxic doses. Overdosage may be dangerous and the physician must select the dosage carefully and continually adjust it in accordance with the needs and response of the patient. As opposed to this, the compounds of the invention have toxic doses which are far in excess of the amounts required to produce a pharmacological effect and present therefore a wide safety margin.

Other known agents exert such a sudden and powerful anti-hypertensive effect that their action is difficult to control. The compounds of the invention do not present this disadvantage. It has, in fact, been observed that the anti-hypertensive action of the compounds of the invention, while being very appreciable, is easy to control.

One compound which may also be cited is the preferred compound of the series described in British Pat. No. 1,380,145, namely 2-(2-ethyl-3-benzofuranyl)-N,N-(3-n-propyl-3-aza-pentamethylene)-acetamidine dihydrochloride.

This compound is chemically related to the compounds of the invention and has been found to be pharmacologically active in the treatment of experimentally induced hypertension. However, it will be seen that the compounds of the invention are not only more active but also far less toxic than the said preferred compound.

Moreover, the anti-hypertensive action of compounds of the invention is exerted with little or no undesirable side-effects while no signs of loss of activity due to habituation have so far been observed.

Finally, it is well known that a diuretic action coupled with an anti-hypertensive action is very useful in the treatment of hypertension, especially when the diuretic action does not provoke excretion of the potassium ion but rather induces excretion of the sodium ion.

The compounds of the invention have been found to present a very favourable sodium-excretion index so that said compounds may be expected to constitute valuable anti-hypertensive agents.

Pharmacological tests have been undertaken with a view to demonstrating the anti-hypertensive effects of the compounds of the invention on different types of experimentally induced hypertension.

The first test was carried out on male rats weighing about 120g in which chronic renal hypertension had been induced by the Grollman technique [Proc. Soc. exp. Biol. Med., 57, 102 (1944)].

According to this technique, the animals are anaesthetized with ether and one kidney is displaced from its site without being detached from the body, the suprarenal gland having been first liberated from the kidney but otherwise left intact. The kidney is then bound with twine in the form of a figure eight, just tightly enough to alter slightly the ellipsoid shape of the organ. Ten days later, the other kidney is completely removed together with its suprarenal gland. About four weeks after the second operation, most of the animals (60 to 70%) develop severe hypertension, systolic pressure in the majority of cases exceeding 180 mm.Hg.

Groups of rats so treated received compounds of the invention in a dose of 25 mg/kg by intragastric route. Arterial pressure was measured immediately before and 1,2,3,4,5 and 6 hours after administration.

The following compounds gave the results indicated:

TABLE I

| Compound | Fall in A.P. (mm.Hg) |
|---|---|
| 2-(2-Ethyl-3-benzofuranyl)-N-(2-morpholino-ethyl)-acetamidoxime | 36 |
| 2-(2-Methyl-3-benzofuranyl)-N-(2-morpholino-ethyl)-acetamidoxime | 25 |
| 2-(2-Ethyl-5-chloro-3-benzofuranyl)-N-(2-morpholino-ethyl)-acetamidoxime | 21 |
| 2-(2-Ethyl-3-benzofuranyl)-N-(2-di-n-butylamine-ethyl)-acetamidoxime | 27 |

In the same test, performed with a well-known anti-hypertensive agent, namely α-methyl-(3,5-dihydroxyphenyl)-alanine, it was found that an intragastric dose of 400 mg/kg of the latter was required to obtain a fall in arterial pressure of between 20 and 30 mm.Hg. Another agent recognized as possessing anti-hypertensive properties, namely hydrochlorothiazide proved to be inactive in this test at a dose of 200 mg/kg given by intragastric route.

The same test was also performed with the preferred compound of British Pat. No. 1,380,145 namely 2-(2-ethyl-3-benzofuranyl)-N,N-(3-n-propyl-3-aza-pentamethylene)-acetamidine dihydrochloride.

At a dose of 50 mg/kg by intragastric route, a fall in arterial pressure of 14 mm.Hg was obtained while a fall of 24 mm.Hg was registered at a dose of 200 mg/kg by the same route.

Further pharmacological tests were carried out with a view to determining the anti-hypertensive activity of the preferred compound of the invention, namely: 2-(2-ethyl-3-benzofuranyl)-N-(2-morpholino-ethyl)-acetamidoxime (or L 9552).

All of these tests were performeed on rats which were in a state of hypertension. Each test was divided into two series. In the first series, one single dose of the product under study was administered by intragastric route to each animal and the arterial pressure of the latter was measured every hour for six hours after administration. In the second series the product under study was given by the same route every day for eleven consecutive days and arterial pressure was measured daily throughout this period. The amount of product administered varied from one animal to another.

The following is an account of the tests so performed.

(1) Rats rendered hypertensive by the GROLLMAN method

When the procedure described above was applied the following results were recorded:

TABLE II

| Type of Treatment | Dose mg/kg | Maximum fall in A.P. (mm.Hg) | Moment of maximum fall in A.P. |
|---|---|---|---|
| Single dose | 10 | 14 | 4th hour |
|  | 25 | 36 | 4th hour |
|  | 50 | 55 | 3rd hour |
| Daily doses (11 days) | 10 | 18 | 6th day |
|  | 25 | 32 | 5th day |
|  | 50 | 47 | 4th day |

(2) Hypertension of endocrine origin

This test was performed in accordance with the technique of STANTON and WHITE (Arch. Int. Pharmacodyn. 154, 351, 1965).

Female rats weighing 90 ± 10g were anaesthetized with ether and hypertension was produced by ablation of one kidney and the corresponding adrenal gland, after which a dose of 50 mg/kg of desoxycorticosterone acetate (DOCA) was administered subcutaneously five days a week over a period of four weeks. Throughout this period the drinking-water given to the rats contained 1% of NaCl. This was replaced by ordinary tap-water when administration of the desoxycorticosterone ceased.

Under these circumstances, arterial pressure rose to about 200 mm.Hg.

The following results were registered:

TABLE III

| Type of Treatment | Dose mg/kg | Maximum fall in A.P. (mm.Hg) | Moment of maximum fall in A.P. |
|---|---|---|---|
| Single dose | 25 | 18 | 4th hour |
|  | 50 | 26 | 4th hour |
|  | 100 | 45 | 4th hour |
| Daily doses | 25 | 15 | 5th day |
|  | 50 | 30 | 4th day |

TABLE III-continued

| Type of Treatment | Dose mg/kg | Maximum fall in A.P. (mm.Hg) | Moment of maximum fall in A.P. |
|---|---|---|---|
| (11 days) | 100 | 49 | 4th day |

(3) Saline hypertension

This test was performed in accordance with the technique of DAHL, KNUDSEN, HEINE and LEITL.

Male rats weighing 55 ± 5g were fed on food containing 8% of NaCl but which was otherwise normal.

After six weeks of this diet, arterial pressure had risen to about 180 mm.Hg.

The following results were registered:

TABLE IV

| Type of Treatment | Dose mg/kg | Maximum fall in A.P. (mm.Hg) | Moment of maximum fall in A.P. |
|---|---|---|---|
| Single dose | 10 | 14 | 4th hour |
|  | 25 | 27 | 4th hour |
|  | 50 | 54 | 4th hour |
| Daily doses (11 days) | 10 | 13 | 7th day |
|  | 25 | 26 | 4th day |
|  | 50 | 53 | 3rd day |

(4) Neurogenic hypertension

This test was performed in accordance with the technique of KRIEGER and IMBS (Circul. Res. 15, 511, 1964 and C.R. Soc. Biol. 162, 778, 1968).

Male rats weighing from 200 to 250g were anaesthetized with ether and 0.5mg of atropine sulphate was administered to them intraperitoneally.

The rats were fixed in a supine position and an incision was made in the front of the neck to expose the neuromuscular bundle comprising the sumpathetic and vagus nerve and the common carotid arteries.

The vagus nerves and the carotid arteries were then carefully isolated while one centimeter was cut out of the sympathetic nerves. The superior laryngeal nerves were severed. The area in which the carotids divide was exposed by pulling aside the appropriate neck muscles (sternocleidomastoideus and omohyoideus). The vessels thus liberated were painted with 10% phenol in ethanol. In this way, complete sympathetic denervation was obtained.

A marked rise in arterial pressure was obtained after 5 to 8 days.

The following results were registered:

TABLE V

| Type of Treatment | Dose mg/kg | Maximum fall in A.P. (mm.Hg) | Moment of maximum fall in A.P. |
|---|---|---|---|
| Single dose | 10 | 18 | 3rd hour |
|  | 25 | 37 | 4th hour |
|  | 50 | 56 | 3rd hour |
| Daily doses (11 days) | 10 | 17 | 5th day |
|  | 25 | 35 | 5th day |

(5) Genetic hypertension

This test was performed in accordance with the technique of OKAMOTO and AOKI (Jap. Circul. J., 27, 282, 1963), using male rats belonging to a race which has been specially bred to produce animals having high blood pressure. The animals employed were about ten weeks old and had a blood pressure reading in the region of 180 mm.Hg.

The following results were obtained:

TABLE VI

| Type of Treatment | Dose mg/kg | Maximum fall in A.P. (mm.Hg) | Moment of maximum fall in A.P. |
|---|---|---|---|
| Single dose | 5 | 16 | 2nd hour |
|  | 10 | 35 | 2nd hour |
|  | 20 | 52 | 3rd hour |
| Daily doses (11 days) | 5 | 0 | — |
|  | 10 | 26 | 4th day |
|  | 20 | 47 | 5th day |

According to PLUMMER (Anti-hypertension agents, p. 67, Edited by SCHLITTLER, Academic Press N.Y. and London, 1967) and many other authors, any substance which is active on the various types of experimentally induced hypertension may be considered as potentially anti-hypertensive in humans.

Moreover, it is now admitted that genetic hypertension constitutes the model of experimental hypertension which is the most closely related to human essential hypertension (which represents 80% of cases of pathological hypertension).

L 9552 has been found to be active in the five types of experimentally induced hypertension employed and especially active in genetic hypertension.

Thus, it may be concluded that L 9552 is most probably active against human hypertension.

Further pharmacological tests were performed in order to determine the diuretic properties of L 9552:

1 — Volumetric urinary excretion

This test was performed according to the technique of LIPSCHITZ et al. (J. Pharmacol. exp. Therap. 79, 97, 1943), by using groups of 20 male albino rats weighing from 150 to 200g which had been deprived of food and drink for 18 hours.

The substance to be tested was given by intragastric route immediately after the intragastric administration of 50 ml/kg of a 9°/₀₀ solution of NaCl.

A control group also of 20 rats only received the saline solution. The total amount of urine excreted during the 6 hours following administration was collected and measured.

The results are expressed in percentage of the volume of saline solution administered and are listed in the following Table:

TABLE VII

| Dose mg/kg | Urinary excretion % |
|---|---|
| 0 | 20 to 50 |
| 10 | 84 |
| 20 | 102 |
| 50 | 118 |
| 100 | 138 |
| 200 | 165 |

The maximum excretion amongst the control animals is 50%, which means that results superior to this value may be considered as signifying a diuretic effect.

2 — Ionic ratio in urinary excretion

This test was performed according to the technique of AMBROSILI et al. (Minerva Nepol. 11,56, 1964).

The substance to be tested was given by intragastric route immediately after the intragastric administration of 50 ml/kg of distilled water to groups of 20 albino male rats weighing 140 { 10g which had been fasting for 18 hours.

A control group, also comprising 20 animals, only received the distilled water.

The total amount of urine excreted during the 4 hours following administration was collected and measured and the total $Na^+$ and $K^+$ ion excretion values determined.

These values were then converted to millieequivalents per liter (mEq/l.) in order to obtain the correct $Na^+$ and $K^+$ ion excretion figures independently of the increase in the amount of urine.

The ionic ratio was obtained according to the following formula:

$$\frac{Na^+}{K^+} \text{ ratio} = \frac{\frac{[Na^+] \text{ of the treated animals}}{[K^+] \text{ of the treated animals}}}{\frac{[Na^+] \text{ of the control animals}}{[K^+] \text{ of the control animals}}}$$

The results were registered:

TABLE VIII

| Dose (mg/kg) | Urinary excretion % | $Na^+$ (mEq/l.) | $K^+$ (mEq/l.) | $Na^+/K^+$ Ratio |
|---|---|---|---|---|
| Control animals | 40 | 27.3 | 18.5 | 1 |
| 10 | 55 | 24.8 | 15.3 | 1.09 |
| 20 | 80 | 43.0 | 17.5 | 1.66 |
| 50 | 95 | 55.6 | 15.0 | 2.50 |
| 100 | 137 | 71.3 | 14.3 | 3.37 |
| 200 | 124 | 78.0 | 15.8 | 3.34 |

These figures show that L 9552 presents a very favourable sodium-excretion index, which is extremely important as far as treatment of hypertension is concerned.

Pharmacological tests were also carried out with a view to showing that L 9552 is devoid of ganglioplegic activity:

(1) The arterial pressure and the tonus of the nictitating membrane of an anaesthetized cat was first noted, after which the contractile reaction of the membrane to an intravenous injection of adrenaline and to electric stimulation of the preganglionic fibre of the cervical sympathetic nerve was tested. It was found that two intravenous doses of 5 mg/kg of L 9552 did not modify the intensity of the contractions of the membrane provoked as described above.

(2) An intravenous dose of 5 mg/kg of L 9552 administered to a dog, which was first anaesthetized with sodium pentobarbital and atropinized, did not alter the hypertensive effect of 1 mg/kg of acetylcholine injected into the vein of the animal. As opposed to this, a ganglioplegic substance such as phenthonium annulled the hypertensive effect of acetylcholine.

Finally, acute toxicity trials were carried out on rats and mice which were kept under observation for 12 days following one single administration.

The following results were registered:

TABLE IX

| Animals | Administration | $LD_0$ (mg/kg) | $LD_{50}$ (mg/kg) | $LD_{95}$ (mg/kg) |
|---|---|---|---|---|
| Mouse | intraperitoneal | 30 | 70 | 110 |
|  | intragastric | 250 | 700 | 1,250 |
| Rat | intraperitoneal | 80 | 200 | 350 |

TABLE IX-continued

| Animals | Administration | LD (mg/kg) | | |
| --- | --- | --- | --- | --- |
| | | $LD_0$ | $LD_{50}$ | $LD_{95}$ |
| | intragastric | 1,100 | 1,900 | 2,500 |

These figures compare very favourably with the intragastric active doses of 50 mg/kg and 100 mg/kg of which the effects are described above and show that there is a very wide safety margin between the toxic dose and the therapeutic dose.

It will be appreciated that, for therapeutic use, the compounds of the invention will normally be administered in the form of a pharmaceutical composition containing as active principle at least one compound of formula I or a pharmaceutically acceptable acid addition salt thereof in association with a pharmaceutical carrier and/or excipient therefor.

Advantageously, for clinical use the composition will be made up in a dosage unit form appropriate to the desired mode of administration, for example a tablet or capsule for oral administration.

The following Examples illustrate the invention.

EXAMPLE 1

2-(2-Ethyl-3-benzofuranyl)-N-(2-morpholino-ethyl)-acetamidoxime sesquioxalate.

(a) Preparation of 2-(2-ethyl-3-benzofuranyl)-acetamidoxime.

To 350 ml. of methanol containing 37.4 g. (0.55 mol) of sodium ethylate were added 38.2 g. (0.55 mol) of hydroxylamine hydrochloride and the reaction medium was stirred until complete dissolution.

Stirring was continued for 16 hours after the addition of 200 ml. of methanol containing 92.6 g. (0.50 mol) of 2-ethyl-3-cyanomethylbenzofuran and the solution was finally refluxed for 3 hours.

The solvent was evaporated off under reduced pressure and the residue obtained was taken up in ether. The ethereal solution was washed with water, dried over anhydrous sodium sulphate and made colourless with active charcoal.

By adding an ethereal solution of hydrochloric acid, 99.7 g. of 2-(2-ethyl-3-benzofuranyl)-acetamidoxime hydrochloride were obtained and recrystallized from a mixture of ethyl acetate and methanol. Yield: 78.3%; m.p. 158°–161° C.

By following the procedure described above and using the appropriate starting products, the compounds listed hereunder were prepared:

| Compound | Melting Point ° C. |
| --- | --- |
| 2-(2-methyl-3-benzofuranyl)-acetamidoxime | 131 – 133 (ethyl acetate/petroleum ether 30/40° C.) |
| 2-(2-methyl-3-benzofuranyl)-acetamidoxime hydrochloride | 190 – 194 (with decomposition) (isopropanol/ethyl ether) |
| 2-(2-n-propyl-3-benzofuranyl)-acetamidoxime hydrochloride | 146 – 150 (methyl ethyl ketone/ethyl ether) |
| 2-(2-isopropyl-3-benzofuranyl)-acetamidoxime hydrochloride | 160 – 162 |
| 2-(2-n-butyl-3-benzofuranyl)-acetamidoxime hydrochloride | 128 – 131 (methyl ethyl ketone/ethyl ether) |
| 2-(2-isobutyl-3-benzofuranyl)-acetamidoxime hydrochloride | 143 – 145 (ethyl acetate/ethanol) |
| 2-[2-(2-butyl)-3-benzofuranyl]-acetamidoxime hydrochloride | 182 – 185 (with decomposition) (methyl ethyl ketone/ethanol/ether) |
| 2-(2-ethyl-5-chloro-3-benzofuranyl)-acetamidoxime hydrochloride | 196 – 199 (with decomposition) (isopropanol) |
| 2-(2-phenyl-3-benzofuranyl)-acetamidoxime | 143 – 145 |
| 2-(2-phenyl-3-benzofuranyl)-acetamidoxime hydrochloride | 203 – 205 (with decomposition) (isopropanol) |

(b) Preparation of 3-(2-ethyl-3-benzofuranyl-methyl)-1,2,4-$\Delta^2$-oxadiazol-5-one.

While stirring, 25.47 g. (0.1 mol) of 2-(2-ethyl-3-benzofuranyl)-acetamidoxime hydrochloride were added to a solution of 13.6 g. (0.2 mol) of sodium ethylate in 250 ml. of absolute ethanol.

After adding 23.6 g. (0.2 mol) of anhydrous diethyl carbonate, the reaction medium was refluxed for 24 hours.

The resulting solution was evaporated to dryness under reduced pressure and the residue obtained was taken up in water.

The aqueous solution so formed was treated with ether and the phases obtained were separated. The aqueous phase was acidified with a dilute solution of hydrochloric acid. The precipitate which was obtained was washed with water and dried under vacuum to give 20 g. of 3-(2-ethyl-3-benzofuranyl-methyl)-1,2,4-$\Delta^2$-oxadiazol-5-one which was recrystallized from a mixture of ether and petroleum ether (40°/60° C.).

Yield: 81.9%; m.p. 156°–159° C.

By following the procedure described above and using the appropriate starting products, the compounds listed hereunder were prepared:

| Compound | Melting Point ° C. |
| --- | --- |
| 3-(2-methyl-3-benzofuranyl-methyl)-1,2,4-$\Delta^2$-oxadiazol-5-one | 162 – 164 |
| 3-(2-n-propyl-3-benzofuranyl-methyl)-1,2,4-$\Delta^2$-oxadiazol-5-one | 155 – 157 |
| 3-(2-isopropyl-3-benzofuranyl-methyl)-1,2,4-$\Delta^2$-oxadiazol-5-one | 162 – 164 |
| 3-(2-n-butyl-3-benzofuranyl-methyl)-1,2,4-$\Delta^2$-oxadiazol-5-one | 157 – 159 |
| 3-(2-isobutyl-3-benzofuranyl-methyl)-1,2,4-$\Delta^2$-oxadiazol-5-one | 134 – 136 (ethyl ether/petroleum ether 40/80° C.) |
| 3-[2-(2-butyl)-3-benzofuranyl-methyl]-1,2,4-$\Delta^2$-oxadiazol-5-one | 117 – 120 (ethyl ether/petroleum ether 40/80° C.) |
| 3-(2-ethyl-5-chloro-3-benzofuranyl-methyl)-1,2,4-$\Delta^2$-oxadiazol-5-one | 169 – 172 (ethyl ether) |
| 3-(2-phenyl-3-benzofuranyl-methyl)-1,2,4-$\Delta^2$-oxadiazol-5-one | 200 – 203 (ethanol) |

(c) Preparation of 3-(2-ethyl-3-benzofuranyl-methyl)-4-(2-morpholino-ethyl)-1,2,4-$\Delta^2$-oxadiazol-5-one.

In a flask equipped with a stirrer and a Soxhlet mounted with a condenser were introduced a solution of 10.5 g. (0.043 mol) of 3-(2-ethyl-3-benzofuranyl-methyl)-1,2,4-$\Delta^2$-oxadiazol-5-one in a mixture of 250 ml. of anhydrous acetone and 50 ml. of methanol, and 7.1 g. (0.051 mol) of finely ground anhydrous potassium carbonate.

In the Soxhlet were introduced 9.3 g. (0.05 mol) of 1-chloro-2-morpholino-ethane hydrochloride.

While stirring, the reaction medium was refluxed for 18 hours. After filtration of the salts, the solution was evaporated off under reduced pressure. The residue obtained was taken up in water and extracted with ether to give 15 g. of 3-(2-ethyl-3-benzofuranyl-methyl)-4-(2- morpholino-ethyl)-1,2,4-$\Delta^2$-oxadiazol-5-one melting at 105°–106° C. Yield: 97.6%.

The melting point of the hydrochloride was 181°–183° C. after recrystallization from a mixture of isopropanol and ethanol.

By following the procedure described above and using the appropriate starting products, the compounds listed hereunder were prepared:

| Compound | Melting Point ° C. |
|---|---|
| 3-(2-ethyl-3-benzofuranyl-methyl)-4-(2-dimethylamino-ethyl)-1,2,4-$\Delta^2$-oxadiazol-5-one hydrochloride | 200 – 204 (methyl ethyl ketone/isopropanol) |
| 3-(2-ethyl-3-benzofuranyl-methyl)-4-(2-diethylamino-ethyl)-1,2,4-$\Delta^2$-oxadiazol-5-one hydrochloride | 166 – 169 (methyl ethyl ketone/isopropanol) |
| 3-(2-ethyl-3-benzofuranyl-methyl)-4-(2-di-n-propylamino-ethyl)-1,2,4-$\Delta^2$-oxadiazol-5-one hydrochloride | 164 – 166 (ethyl acetate/acetone) |
| 3-(2-ethyl-3-benzofuranyl-methyl)-4-(2-di-n-butylamino-ethyl)-1,2,4-$\Delta^2$-oxadiazol-5-one monohydrated oxalate | 108 – 112 (ethyl acetate) |
| 3-(2-ethyl-3-benzofuranyl-methyl)-4-(2-pyrrolidino-ethyl)-1,2,4-$\Delta^2$-oxadiazol-5-one hydrochloride | 188 – 190 (with decomposition) (isopropanol) |
| 3-(2-ethyl-3-benzofuranyl-methyl)-4-(3-pyrrolidino-n-propyl)-1,2,4-$\Delta^2$-oxadiazol-5-one hydrochloride | 169 – 171 (methyl ethyl ketone) |
| 3-(2-ethyl-3-benzofuranyl-methyl)-4-(2-piperidino-ethyl)-1,2,4-$\Delta^2$-oxadiazol-5-one hydrochloride | 177 – 180 (isopropanol) |
| 3-(2-ethyl-3-benzofuranyl-methyl)-4-(3-piperidino-n-propyl)-1,2,4-$\Delta^2$-oxadiazol-5-one hydrochloride | 172 – 175 (isopropanol/ethyl ether) |
| 3-(2-ethyl-3-benzofuranyl-methyl)-4-(3-morpholino-n-propyl)-1,2,4-$\Delta^2$-oxadiazol-5-one hydrochloride | 119 – 122 (acetone/ethyl ether) |
| 3-(2-ethyl-3-benzofuranyl-methyl)-4-(2-heptamethyleneimino-ethyl)-1,2,4-$\Delta^2$-oxadiazol-5-one | 74 – 75 (isopropyl ether) |
| 3-(2-ethyl-3-benzofuranyl-methyl)-4-(2-heptamethyleneimino-ethyl)-1,2,4-$\Delta^2$-oxadiazol-5-one hydrochloride salt | 199 – 201 (ethyl acetate/methyl alcohol) |
| 3-(2-ethyl-3-benzofuranyl-methyl)-4-(3-di-n-propylamino-n-propyl)-1,2,4-$\Delta^2$-oxadiazol-5-one oxalate | 122 – 125 (ethyl acetate/methyl alcohol) |
| 3-(2-ethyl-3-benzofuranyl-methyl)-4-[2-(4-n-propyl-piperazino)-ethyl]-1,2,4-$\Delta^2$-oxadiazol-5-one dihydrochloride | 228 – 232 (with decomposition) (isopropyl alcohol/methyl alcohol) |
| 3-(2-ethyl-3-benzofuranyl-methyl)-4-[2-(4-methyl-piperazino)-ethyl]-1,2,4-$\Delta^2$-oxadiazol-5-one dihydrochloride | 230 – 233 (with decomposition) (methyl alcohol) |
| 3-(2-ethyl-5-chloro-3-benzofuranyl-methyl)-4-(2-pyrrolidino-ethyl)-1,2,4-$\Delta^2$-oxadiazol-5-one hydrochloride | 211 – 214 (with decomposition) (isopropyl alcohol/methanol) |
| 3-(2-ethyl-5-chloro-3-benzofuranyl-methyl)-4-(2-piperidino-ethyl)-1,2,4-$\Delta^2$-oxadiazol-5-one hydrochloride | 205 – 208 (ethyl acetate/methanol) |
| 3-(2-ethyl-5-chloro-3-benzofuranyl-methyl)-4-(2-morpholino-ethyl)-1,2,4-$\Delta^2$-oxadiazol-5-one hydrochloride | 225 – 229 (with decomposition) (ethyl acetate/methanol) |
| 3-(2-methyl-3-benzofuranyl-methyl)-4-(2-morpholino-ethyl)-1,2,4-$\Delta^2$-oxadiazol-5-one | 130 – 132 (ethyl ether) |
| 3-(2-n-propyl-3-benzofuranyl-methyl)-4-(2-morpholino-ethyl)-1,2,4-$\Delta^2$-oxadiazol-5-one oxalate | 145 – 148 (isopropyl alcohol) |
| 3-(2-isopropyl-3-benzofuranyl-methyl)-4-(2-pyrrolidino-ethyl)-1,2,4-$\Delta^2$-oxadiazol-5-one hydrochloride | 220 – 223 (isopropyl alcohol/ethanol) |
| 3-(2-isopropyl-3-benzofuranyl-methyl)-4-(2-piperidino-ethyl)-1,2,4-$\Delta^2$-oxadiazol-5-one hydrochloride | 217 – 221 (with decomposition) (methanol/ethyl ether) |
| 3-(2-isopropyl-3-benzofuranyl-methyl)-4-(2-morpholino-ethyl)-1,2,4-$\Delta^2$-oxadiazol-5-one hydrochloride | 211 – 214 (with decomposition) (methanol) |
| 3-(2-n-butyl-3-benzofuranyl-methyl)-4-(2-piperidino-ethyl)-1,2,4-$\Delta^2$-oxadiazol-5-one hydrochloride | 174 – 176 (isopropanol/ethyl ether) |
| 3-(2-n-butyl-3-benzofuranyl-methyl)-4-(2-morpholino-ethyl)-1,2,4-$\Delta^2$-oxadiazol-5-one hydrochloride | 185 – 188 (isopropanol/methanol/ethyl ether) |
| 3-(2-isobutyl-3-benzofuranyl-methyl)-4-(2-morpholino-ethyl)-1,2,4-$\Delta^2$-oxadiazol-5-one hydrochloride | 185 – 189 (methanol/ethyl ether) |
| 3-(2-phenyl-3-benzofuranyl-methyl)-4-(2-morpholino-ethyl)-1,2,4-$\Delta^2$-oxadiazol-5-one | 140 – 142 (ethanol) |
| 3-(2-phenyl-3-benzofuranyl-methyl)-4-(2-piperidino-ethyl)-1,2,4-$\Delta^2$-oxadiazol-5-one hydrochloride | 208 – 211 (ethanol) |
| 3-[2-(2-n-butyl)-3-benzofuranyl-methyl]-4-(2-morpholino-ethyl)-1,2,4-$\Delta^2$-oxadiazol-5-one hydrochloride | 211 – 215 (with decomposition) (isopropanol/methanol) |

(d) Preparation of 2-(2-ethyl-3-benzofuranyl)-N-(2-morpholino-ethyl)-acetamidoxime.

To a solution of 7.9 g. (0.02 mol) of 3-(2-ethyl-3-benzofuranyl-methyl)-4-(2-morpholino-ethyl)-1,2,4-$\Delta^2$-oxadiazol-5-one hydrochloride in 70 ml. of methanol was added a solution of 3.2 g. (0.08 mol) of sodium hydroxide in 32 ml. of water.

The reaction medium was refluxed for 30 minutes and was evaporated under reduced pressure until three quarters of the volume were eliminated.

The resulting residue was taken up in 200 ml. of water and the pH of the reaction medium was adjusted to 8.

The solution so formed was extracted with ether to give 5.89 g. of 2-(2-ethyl-3-benzofuranyl)-N-(2-morpholinoethyl)-acetamidoxime which represented a yield of 89%. The crude product was taken up in a small quantity of methanol and, while stirring, was acidified by means of a methanol solution containing 3 g. (0.33 mol) of oxalic acid to give 8 g. of 2-(2-ethyl-3-benzofuranyl)-N-(2-morpholino-ethyl)-acetamidoxime sesquioxalate. Yield: 85%; m.p. 163°–164° C.

By following the procedure described above and using the appropriate starting products, the compounds listed hereunder were prepared:

| Compound | Melting Point ° C. |
|---|---|
| 2-(2-ethyl-3-benzofuranyl)-N-(2-dimethylamino-ethyl)-acetamidoxime dihydrochloride | 161 – 163 (methyl ethyl ketone/isopropanol) |
| 2-(2-ethyl-3-benzofuranyl)-N-(2-diethylamino-ethyl)-acetamidoxime sesquioxalate | 159 – 161 (with decomposition) (ethanol) |
| 2-(2-ethyl-3-benzofuranyl)-N-(2-di-n-propylamino-ethyl)-acetamidoxime dihydrochloride | 180 – 184 (with decomposition) (ethyl acetate/methanol) |
| 2-(2-ethyl-3-benzofuranyl)-N-(2-di-n-butylamino-ethyl)-acetamidoxime dihydrochloride | 165 – 168 (ethyl acetate/methanol) |
| 2-(2-ethyl-3-benzofuranyl)-N-(2-pyrrolidino-ethyl)-acetamidoxime dihydrochloride | 184 – 187 (with decomposition) (methyl ethyl ketone/isopropanol) |
| 2-(2-ethyl-3-benzofuranyl)-N-(3-pyrrolidino-n-propyl)-acetamidoxime | 79 – 82 (n-hexane/petroleum ether 40/60° C.) |
| 2-(2-ethyl-3-benzofuranyl)-N-(2-piperidino-ethyl)-acetamidoxime dihydrochloride | 181 – 183 (with decomposition) (ethyl acetate/isopropanol) |
| 2-(2-ethyl-3-benzofuranyl)-N-(3-piperidino-n-propyl)-acetamidoxime hydrochloride | 171 – 173 (with decomposition) (isopropanol/ethyl ether) |
| 2-(2-ethyl-3-benzofuranyl)-N-(3-morpholino-n-propyl)-acetamidoxime dihydrochloride | 199 – 202 (isopropanol/ethyl ether) |
| 2-(2-ethyl-3-benzofuranyl)-N- | 79 – 81 |

-continued

| Compound | Melting Point ° C. |
| --- | --- |
| (2-heptamethyleneimino-ethyl)-acetamidoxime | (n-hexane) |
| 2-(2-ethyl-3-benzofuranyl)-N-(3-di-n-propylamino-n-propyl)-acetamidoxime dioxalate | 123 – 126 (with decomposition) (ethyl acetate/methanol) |
| 2-(2-ethyl-3-benzofuranyl)-N-[2-(4-methyl-piperazino)-ethyl]-acetamidoxime | 121 – 123 (ethanol/water) |
| 2-(2-ethyl-3-benzofuranyl)-N-[2-(4-n-propyl-piperazino)-ethyl]-acetamidoxime trihydrochloride | 161 – 165 (ethanol/ethyl ether) |
| 2-(2-ethyl-5-chloro-3-benzofuranyl)-N-(2-pyrrolidino-ethyl)-acetamidoxime dihydrochloride | 210 – 213 (with decomposition) (isopropanol) |
| 2-(2-ethyl-5-chloro-3-benzofuranyl)-N-(2-piperidino-ethyl)-acetamidoxime | 118 – 120 (petroleum ether 40/80° C.) |
| 2-(2-ethyl-5-chloro-3-benzofuranyl)-N-(2-piperidino-ethyl)-acetamidoxime dihydrochloride | 157 – 160 (with decomposition) (ethyl acetate/methanol) |
| 2-(2-ethyl-5-chloro-3-benzofuranyl)-N-(2-morpholino-ethyl)-acetamidoxime | 110 – 112 (petroleum ether 60/80° C.) |
| 2-(2-ethyl-5-chloro-3-benzofuranyl)-N-(2-morpholino-ethyl)-acetamidoxime dihydrochloride | 122 – 126 (with decomposition) (ethyl acetate/methanol) |
| 2-(2-methyl-3-benzofuranyl)-N-(2-morpholino-ethyl)-acetamidoxime sesquioxalate | 148 – 150 (with decomposition) methanol/ethyl ether) |
| 2-(2-n-propyl-3-benzofuranyl)-N-(2-morpholino-ethyl)-acetamidoxime sesquioxalate | 162 – 164 (with decomposition) (methanol) |
| 2-(2-isopropyl-3-benzofuranyl)-N-(2-pyrrolidino-ethyl)-acetamidoxime dihydrochloride | 201 – 202 (with decomposition) (isopropanol) |
| 2-(2-isopropyl-3-benzofuranyl)-N-(2-piperidino-ethyl)-acetamidoxime dihydrochloride | 180 – 184 (ethyl acetate/isopropanol) |
| 2-(2-isopropyl-3-benzofuranyl)-N-(2-morpholino-ethyl)-acetamidoxime dihydrochloride | 196 – 199 (with decomposition) (acetone/isopropanol) |
| 2-(2-n-butyl-3-benzofuranyl)-N-(2-piperidino-ethyl)-acetamidoxime | 72 – 74 (petroleum ether 40/80° C.) |
| 2-(2-n-butyl-3-benzofuranyl)-N-(2-morpholino-ethyl)-acetamidoxime sesquioxalate | 115 (with decomposition) (methanol) |
| 2-(2-isobutyl-3-benzofuranyl)-N-(2-morpholino-ethyl)-acetamidoxime dihydrochloride | 172 – 174 (ethanol/ethyl ether) |
| 2-[2-(2-n-butyl)-3-benzofuranyl]-N-(2-morpholino-ethyl)-acetamidoxime dihydrochloride | 197 – 199 (with decomposition) (isopropanol) |
| 2-(2-phenyl-3-benzofuranyl)-N-(2-morpholino-ethyl)-acetamidoxime sesquioxalate | 157 – 159 (ethanol) |
| 2-(2-phenyl-3-benzofuranyl)-N-(2-piperidino-ethyl)-acetamidoxime | 162 – 164 (ether) |

EXAMPLE 2

2-(2-Ethyl-3-benzofuranyl)-2,2-dimethyl-N-(2-morpholino-ethyl)-acetamidoxime.

(a) Preparation of 2-(2-ethyl-3-benzofuranyl)-2-methylpropionitrile.

While stirring, a solution of 37 g. (0.2 mol) of 2-ethyl-3-cyanomethyl-benzofuran in 200 ml. of anhydrous ethyl ether was added, drop-by-drop, to a suspension of 17.2 g. (0.44 mol) of sodium amide in 250 ml. of anhydrous ethyl ether.

Stirring was continued for 2 hours at room temperature and then a solution of 85.2 g. (0.6 mol) of methyl iodide in 200 ml. of anhydrous ethyl ether was added drop-by-drop. Any excess of sodium amide was decomposed by adding a little water and the solution obtained was poured into water.

The resulting aqueous solution was extracted with ether and 22.45 g. of 2-(2-ethyl-3-benzofuranyl)-2-methylpropionitrile were obtained.

Yield: 52.7%; b.p. 95°–100° C. (0.03 mm Hg).

(b) Preparation of 2-(2-ethyl-3-benzofuranyl)-2,2-dimethylacetamidoxime.

The above-named compound was prepared from 2-(2-ethyl-3-benzofuranyl)-2-methyl-propionitrile by the procedure described in Example 1(a), but using 1.5 mol of hydroxylamine hydrochloride and sodium methylate for each mole of 2-(2-ethyl-3-benzofuranyl)-2-methylpropionitrile and continuing the reaction for 72 hours. Yield: 41%; m.p. 118°–120° C. after recrystallization from a mixture of ethyl acetate and light petroleum ether.

Melting point of the hydrochloride: 189°–192° C. after recrystallization from a mixture of ethyl acetate, isopropanol and ethyl ether.

(c) Preparation of 3-[1-(2-ethyl-3-benzofuranyl)-1-methyl-1-ethyl]-1,2,4-$\Delta^2$-oxadiazol-5-one The above-named compound was prepared from 2-(2-ethyl-3-benzofuranyl)-2,2-dimethyl-acetamidoxime hydrochloride by the procedure described in Example 1(b).

Melting point: 153°–156° C.

(d) Preparation of 3-[1-(2-ethyl-3-benzofuranyl)-1-methyl-1-ethyl]-4-(2-morpholino-ethyl)-1,2,4-$\Delta^2$-oxadiazol-5-one The above-named compound was prepared from 3-[1-(2-ethyl-3-benzofuranyl)-1-methyl-1-ethyl]-1,2,4-$\Delta^2$-oxadiazol-5-one by the procedure described in Example 1(c).

Melting point of the hydrochloride: 215°–219° C. after recrystallization from a mixture of methyl ethyl ketone, isopropyl alcohol and ethyl ether.

By following the same procedure and using the appropriate starting-products, the compound cited hereunder was prepared: 3-[1-(2-ethyl-3-benzofuranyl)-1-methyl-1-ethyl]-4-(2-piperidino-ethyl)-1,2,4-$\Delta^2$-oxadiazol-5-one.

Melting point of the hydrochloride: 209°–213° C. (decomposition) after recrystallization from a mixture of acetone, isopropanol and ethyl ether.

(e) Preparation of 2-(2-ethyl-3-benzofuranyl)-2,2-dimethyl-N-(2-morpholino-ethyl)-acetamidoxime The above-named compound was prepared from 3-[1-(2-ethyl-3-benzofuranyl)-1-methyl-1-ethyl]-4-(2-morpholino-ethyl)-1,2,4-$\Delta^2$-oxadiazol-5-one hydrochloride by the procedure described in Example 1(d).

Melting point: 110°–112° C. after recrystallization from n-hexane.

By following the same procedure and using the appropriate starting-products, the compound cited hereunder was prepared: 2-(2-ethyl-3-benzofuranyl)-2,2-dimethyl-N-(2-piperidino-ethyl)acetamidoxime. Melting point: 94°–97° C. after recrystallization from a mixture of ethyl ether and petroleum ether boiling from 40° to 60° C.

15

EXAMPLE 3

2-(2-ethyl-3-benzofuranyl)-2-ethyl-N-(2-morpholino-ethyl)acetamidoxime

(a) Preparation of 2-(2-ethyl-3-benzofuranyl)-butyronitrile

While stirring, 8.3g (0.106 mol) of a 50%- suspension of sodium amide in toluene, which was taken up in 50ml of ethyl ether, was added, drop-by-drop, to a solution of 18.52g (0.1 mol) of (2-ethyl-3-benzofuranyl)-acetonitrile in 200ml of dry ether. The mixture was refluxed for one hour and was allowed to cool to room-temperature. Stirring was continued and a solution of 23g (0.1475 mol) of ethyl iodide in 100ml of ethyl ether was added drop-by-drop. The reaction medium was refluxed for 3 hours and was allowed to cool.

Any excess of sodium amide was carefully decomposed by adding a little water and the medium was poured into water. The nitrile was extracted with ether and isolated. Yield: 75%. Boiling point: 115°–117° C. (0.5 mm. Hg)

(b) Preparation of 2-(2-ethyl-3-benzofuranyl)-butyramidoxime

The above-named compound was prepared from 2-(2-ethyl-3-benzofuranyl)-butyronitrile by the procedure described in Example 1(a). Melting point of the hydrochloride: 160°–163° C. after recrystallization from ethyl acetate.

(c) Preparation of 3-[1-(2-ethyl-3-benzofuranyl)-1-propyl]-1,2,4-$\Delta^2$-oxadiazol-5-one The above-named compound was prepared from 2-(2-ethyl-3-benzofuranyl)-butyramidoxime by the procedure described in Example 1(b).

Melting point: 130°–132° C. after recrystallization from ethyl ether and petroleum ether 40°/60°.

(d) Preparation of 3-[1-(2-ethyl-3-benzofuranyl)-1-propyl]-4-(2-morpholino-ethyl)-1,2,4-$\Delta^2$-oxadiazol-5-one The above-named compound was prepared from 3-[1-(2-ethyl-3-benzofuranyl)-1-propyl]-1,2,4-$\Delta^2$-oxadiazol-5-one by the procedure described in Example 1(c).

Melting point of the hydrochloride: 185°–188° C. after recrystallization from isopropanol.

(e) Preparation of 2-(2-ethyl-3-benzofuranyl)-2-ethyl-N-(2-morpholinoethyl)-acetamidoxime The above-named compound was prepared from 3-[1-(2-ethyl-3-benzofuranyl)-1-propyl]-4-(2-morpholino-ethyl)-1,2,4-$\Delta^2$-oxadiazol-5-one by the procedure described in Example 1 (d).

Melting point of the sesquioxalate : 139° – 141° C. (decomposition) after recrystallization from isopropanol.

EXAMPLE 4

2-(2-ethyl-3-benzofuranyl)-2-methyl-N-(2-morpholino-ethyl)-acetamidoxime

(a) Preparation of 2-(2-ethyl-3-benzofuranyl)-methyl propionate

While stirring, 1g of ferric nitrite was added to 500ml of liquid ammonia followed by 6.35g (0.276 at.g.) of sodium. Stirring was continued for 30 minutes and a solution of 54.5g (0.25 mol) of (2-ethyl-3-benzofuranyl)-methyl acetate in 50ml of dry ethyl ether was added drop-by-drop. Stirring was continued for 2 hours and a solution of 39g (0.275 mol) of methyl iodide in 50ml of dry ether were added drop-by-drop.

The reaction medium was allowed to cool to room-temperature while being stirred for 2 hours.

100g of ammonium chloride were added to the brownish residue and the medium was extracted four or five times with ethyl ether. The organic phases were collected, washed with water and dried over anhydrous sodium sulphate. The ether was evaporated off and 21.4g of 2-(2-ethyl-3-benzofuranyl)-methyl propionate were obtained.

Yield : 37%. Boiling point : 100° C. (0.4 mm.Hg).

(b) Preparation of 2-(2-ethyl-3-benzofuranyl)-propionic acid 41.6g (0.179 mol) of 2-(2-ethyl-3-benzofuranyl)-methyl propionate were added to a solution of 12g (0.215 mol) of potassium hydroxide in a mixture of 240ml of water and 120ml of methanol. The reaction medium was heated for 3 hours over a water-bath and the methanol was evaporated off. The aqueous solution was acidified with hydrochloric acid and was extracted with ether. The ethereal solution was dried over anhydrous sodium sulphate and the solvent was evaporated off to give 39g of 2-(2-ethyl-3-benzofuranyl)-propionic acid.

Yield : 90%. Melting point : 62° – 64° C. after recrystallization from petroleum ether 40° – 60°.

(c) Preparation of 2-(2-ethyl-3-benzofuranyl)-propionamide

A solution of 35.1g (0.161 mol) of 2-(2-ethyl-3-benzofuranyl)-propionic acid in 100ml of thionyl chloride was stirred for 12 hours at room-temperature, then for one hour at the temperature of the water-bath.

The excess of thionyl chloride was evaporated off under reduced pressure and the 2-(2-ethyl-3-benzofuranyl)-propionic acid chloride which formed was dissolved in 100ml of dry ether and the resulting solution was added, drop-by-drop, to 500ml of ethyl ether saturated with dry ammonia.

The reaction medium was stirred for 1 hour and was allowed to stand for 12 hours. The ethereal solution was washed with water, dried over anhydrous sodium sulphate and the solvent was evaporated off to give 35g of 2-(2-ethyl-3-benzofuranyl)-propionamide.

Yield : 100%. Melting point : 84° – 87° C. after recrystallization from n-hexane.

(d) Preparation of 2-(2-ethyl-3-benzofuranyl)-propionitrile

A solution of 35g (0.16 mol) of 2-(2-ethyl-3-benzofuranyl)-propionamide in 500ml of toluene was refuxed for 18 hours in the presence of $P_2O_5$. The organic phase was decanted off and the residue was carefully decomposed with iced water and extracted with ether.

The organic phase was washed with water, dried over sodium sulphate and added to the toluenic phase.

The solvents were evaporated off under reduced pressure and the residue was fractionated to give 23.8g of 2-(2-ethyl-3-benzofuranyl)-propionitrile.

Yield : 74.4%. Boiling point : 105° C. (0.2 mm.Hg).

(e) Preparation of 2-(2-ethyl-3-benzofuranyl)-propionamidoxime

The above-named compound was prepared from 2-(2-ethyl-3-benzofuranyl)-propionitrile by the procedure described in Example 2 (b).

Melting point of the hydrochloride : 152° – 155° C. after recrystallization from acetone-ethyl ether.

(f) Preparation of 3-[1-(2-ethyl-3-benzofuranyl)-1-ethyl]-1,2,4-Δ²-oxadiazol-5-one The above-named compound was prepared from 2-(2-ethyl-3-benzofuranyl)-propionamidoxime by the procedure described in Example 1 (b)

Melting point : 110° – 113° C. after recrystallization from ethyl etherpetroleum ether 40° – 60°.

(g) Preparation of 3-[1-(2-ethyl-3-benzofuranyl)-1-ethyl]-4-(2-morpholino-ethyl)-1,2,4-Δ²-oxadiazol-5-one The above-named compound was prepared from 3-[1-(2-ethyl-3-benzofuranyl)-1-ethyl]-1,2,4-Δ²-oxidiazol-5-one by the procedure described in Example 1 (c).

Melting point : 132° – 135° C. after recrystallization from isopropanolisopropyl ether.

(h) Preparation of 2-(2-ethyl-3-benzofuranyl)-2-methyl-N-(2-morpholino-ethyl)-acetamidoxime The above-named compound was prepared from 3-[1-(2-ethyl-3-benzofuranyl)-1-ethyl]-4-(2-morpholino-ethyl)-1,2,4-Δ²-oxadiazol-5-one by the procedure described in Example 1 (d).

Melting point : 112° – 115° C. after recrystallization from acetonepetroleum ether 40° – 60°.

Melting point of the sesquioxalate : 132° – 135° C. (decomposition). after recrystallization from methanol-ethyl ether.

EXAMPLE 5

Hard-gelatine capsules were prepared in accordance with known pharmaceutical techniques:

| Ingredients | mg per capsule | |
|---|---|---|
| | 1 | 2 |
| 2-(2-ethyl-3-benzofuranyl)-N-(2-morpholino-ethyl)-acetamidoxime sesquioxalate | 20 | 10 |
| corn starch | 194.3 | 204.3 |
| colloidal silica | 0.7 | 0.7 |
| | 215.0 mg | 215.0 mg |

We claim:

1. Compounds of the general formula:

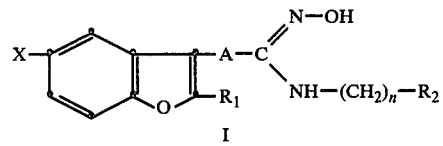

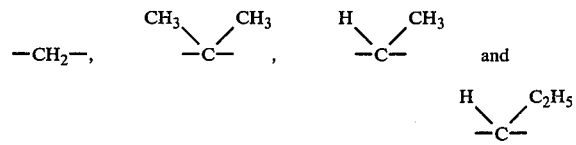

and the pharmaceutically acceptable acid addition salts thereof, wherein $R_1$ represents a branched- or straight-chain alkyl group containing from 1 to 4 carbon atoms or a phenyl group, A represents one of the groups:

$-CH_2-$, $\overset{CH_3}{\underset{-C-}{\diagdown}}\overset{CH_3}{\diagup}$, $\overset{H}{\underset{-C-}{\diagdown}}\overset{CH_3}{\diagup}$ and $\overset{H}{\underset{-C-}{\diagdown}}\overset{C_2H_5}{\diagup}$ $R_2$ represents a dimethylamino, diethylamino, di-n-propylamino, di-n-butylamino, pyrrolidino, morpholino, piperidino or heptamethyleneimino group or a 1-piperazino group substituted in the 4-position by a straight-chain alkyl group containing from 1 to 4 carbon atoms, X represents a hydrogen or chlorine atom or a methoxy group and $n$ is the integer 2 or 3.

2. 2-(2-ethyl-3-benzofuranyl)-N-(2-morpholino-ethyl)-acetamidoxime and its pharmaceutically acceptable acid addition salts.

3. An anti-hypertensive pharmaceutical composition containing an essential active principle an effective amount of at least one compound or a pharmaceutically acceptable acid addition salt thereof as claimed in claim 1 in association with a pharmaceutical excipient therefor.

4. An anti-hypertensive pharmaceutical composition containing an essential active principle an effective amount of 2-(2-ethyl-3-benzofuranyl)-N-(2-morpholino-ethyl)-acetamidoxime or a pharmaceutically acceptable acid addition salt thereof in association with a pharmaceutical excipient therefor.

5. A composition as claimed in claim 3 in a dosage unit form suitable for oral administration.

6. Method of treating hypertension in a subject in need of such treatment, said method consisting in administering to the said subject an effective amount of at least one compound of formula I as defined by claim 1 or a pharmaceutically acceptable acid addition salt thereof.

7. 2-(2-Methyl-3-benzofuranyl)-N-(2-morpholino-ethyl)-acetamidoxime and its pharmaceutically acceptable acid addition salts.

8. 2-(2-Ethyl-5-chloro-3-benzofuranyl)-N-(2-morpholino-ethyl)-acetamidoxime and its pharmaceutically acceptable acid addition salts.

9. 2-(2-Ethyl-3-benzofuranyl)-N-(2-di-n-butylaminoethyl)-acetamidoxime and its pharmaceutically acceptable acid addition salts.

* * * * *

UNITED STATES PATENT OFFICE
CERTIFICATE OF CORRECTION

Patent No. 4,124,710　　　　　Dated November 7, 1978

Inventor(s) Marcel Descamps and Alex Areschka

It is certified that error appears in the above-identified patent and that said Letters Patent are hereby corrected as shown below:

First page, first column, below item [22], the following is inserted:

--[30] Foreign Application Priority Data
December 22, 1975 [GB] United Kingdom
52475/75--;

Claim 3, line 2, "an" should read --as--;
Claim 4, line 2, "an" should read --as--.

Signed and Sealed this

Eighth Day of January 1980

[SEAL]

Attest:

SIDNEY A. DIAMOND

Attesting Officer　　Commissioner of Patents and Trademarks